(12) United States Patent
Lechner et al.

(10) Patent No.: US 8,939,995 B2
(45) Date of Patent: Jan. 27, 2015

(54) RADIOLUCENT REFERENCE FOR COMPUTER-ASSISTED SURGERY

(75) Inventors: Christian Lechner, Jesenwang (DE); Rupert Heigl, München (DE)

(73) Assignee: Brainlab AG, Feldkirchen (DE)

( * ) Notice: Subject to any disclaimer, the term of this patent is extended or adjusted under 35 U.S.C. 154(b) by 1588 days.

(21) Appl. No.: 12/175,035

(22) Filed: Jul. 17, 2008

(65) Prior Publication Data

US 2009/0024127 A1     Jan. 22, 2009

Related U.S. Application Data (60) Provisional application No. 60/951,489, filed on Jul. 24, 2007.

(30) Foreign Application Priority Data

Jul. 17, 2007   (EP) .................................... 07112624

(51) Int. Cl.
A61B 19/00 (2006.01)
A61L 31/12 (2006.01)
A61B 17/00 (2006.01)

(52) U.S. Cl.
CPC ............... *A61L 31/126* (2013.01); *A61B 19/54* (2013.01); *A61B 2017/00915* (2013.01); *A61B 2017/0092* (2013.01); *A61B 2019/5483* (2013.01)
USPC ............ 606/130; 606/206; 606/217; 606/191

(58) Field of Classification Search
CPC ............... A61B 19/54; A61B 2017/00915; A61B 2017/0092; A61B 2019/5483; A61B 19/20; A61B 19/201; A61B 19/26; A61L 31/126

USPC ............. 606/86, 102–103, 53, 54, 56, 60–62, 606/130, 300, 205–208, 210, 211, 217, 220, 606/191, 192; 128/898–899; 81/300, 313, 81/341, 342

See application file for complete search history.

(56) References Cited

U.S. PATENT DOCUMENTS

| 2,249,906 | A | * | 7/1941 | Longoria ...................... 606/166 |
| 3,136,040 | A | * | 6/1964 | Bauer et al. ..................... 29/739 |
| 4,174,715 | A | * | 11/1979 | Hasson ......................... 606/206 |
| 5,249,574 | A | * | 10/1993 | Bush et al. ........................ 607/9 |
| 5,637,110 | A | * | 6/1997 | Pennybacker et al. .......... 606/46 |
| 6,221,035 | B1 | * | 4/2001 | Kana et al. ...................... 602/16 |
| 6,226,548 | B1 | | 5/2001 | Foley et al. |
| 6,235,027 | B1 | * | 5/2001 | Herzon ........................... 606/51 |
| 6,283,965 | B1 | * | 9/2001 | Ballier ............................ 606/59 |
| 6,837,892 | B2 | | 1/2005 | Shoham |

(Continued)

FOREIGN PATENT DOCUMENTS

| EP | 0171884 | A1 | * | 6/1985 | .................... 606/130 |
| EP | 0 171 884 | A | | 2/1986 | |

(Continued)

*Primary Examiner* — Katherine Dowe
*Assistant Examiner* — Sidharth Kapoor
(74) *Attorney, Agent, or Firm* — Tucker Ellis LLP (57) ABSTRACT

A radiolucent fastening device for fastening a reference device to a body for computer-assisted surgery, wherein a part of the fastening device is made from an unsubstituted carbon fiber reinforced polyether compound, a monosubstituted carbon fiber reinforced polyether compound or a multisubstituted carbon fiber reinforced polyether compound.

19 Claims, 10 Drawing Sheets

(56) References Cited

U.S. PATENT DOCUMENTS

| | | |
|---|---|---|
| 2005/0065515 A1 | 3/2005 | Jahng |
| 2005/0113841 A1* | 5/2005 | Sheldon et al. ............ 606/88 |
| 2006/0009780 A1 | 1/2006 | Foley et al. |
| 2006/0020271 A1* | 1/2006 | Stewart et al. ............ 606/139 |

FOREIGN PATENT DOCUMENTS

| | | |
|---|---|---|
| EP | 1 238 637 A | 9/2002 |
| EP | 1 967 155 | 9/2008 |
| GB | 2 405 342 A | 3/2005 |
| WO | 2004/075767 | 9/2004 |

* cited by examiner

Fig. 2
Conventional

RADIOLUCENT REFERENCE FOR COMPUTER-ASSISTED SURGERY

RELATED APPLICATION DATA

This application claims priority of U.S. Provisional Application No. 60/951,489 filed on Jul. 24, 2007, and EP 07 112624 filed on Jul. 17, 2007, which are incorporated herein by reference in their entirety.

FIELD OF THE INVENTION

The invention relates generally to a fastening device for attaching or securing a reference device to a part of a patient's body, such as a bone, to be used in computer-assisted surgery and/or during other medical procedures.

BACKGROUND OF THE INVENTION

Fastening devices for attaching reference devices to a part of a body for computer-assisted medical procedures are known. Such reference devices may be attached, for example, to a bone. The fastening devices may be configured in various different designs. Examples include clamps and/or forceps with pointed portions such as spikes that penetrate a body or bone when being fastened. Rod-shaped devices having screws that secure a reference device to a body or bone also are known, as well as plate shaped fastening devices that are fastened to a body or bone by a number of screws.

In the field of computer-assisted surgery, a reference device may be attached to each of various fastening devices. The reference device may be an array including markers that are used for navigation in computer-assisted operations. The markers can be active markers that emit radiation that is detected by a camera system in an operating room. The markers also can be passive markers such that they reflect radiation that is detected by a camera system in the operating room. If a surgeon chooses to use computer or navigational assistance in connection with a treatment tool to be navigated (for example, a surgical instrument) the surgeon may attach a reference device to the instrument. When the reference device of the instrument apparatus is detected by the camera system at the same time as the reference device of the body, the position of the instrument relative to the position of the body may be determined.

Operations that require a high level of precision are often performed with computer assistance. For this reason, it is important for the reference device to be securely fixed or attached to the bone or other body part. The fastening device for securing the reference device to the bone should not be inadvertently detached or broken and, thus, should be designed to withstand high mechanical stresses. For this reason, and for the reason that the devices should be reusable and sterilizable, conventional fastening devices are often made of high-grade steel or titanium.

Another characteristic of fastening devices is their size. Surgeons often desire a smaller fastening device so that it does not interfere with a computer-assisted operation. A smaller device does not obstruct the surgeon's freedom of movement and field of vision.

Operations requiring a high level of precision often may be accompanied by imaging methods, including intra-operative imaging. Accordingly, a recording may be taken (for example, using a CT scanner or an MRT scanner) during an operation, wherein it is important to obtain high-quality scan recordings. The use of certain fastening device materials may cause distortion or artifacts in the recordings. Metals are generally radio-opaque as well as some ceramics, whereas plastics are generally radio-translucent. Accordingly, conventional fastening devices made of high-grade steel and titanium alloys may cause numerous artifacts.

The imaging methods can be various types of x-ray recordings (two-dimensional x-rays, three-dimensional x-rays, or three-dimensional computer tomography). In this respect, it is noted that artifact formation in two-dimensional x-ray recordings is different than artifact formation in three-dimensional x-ray recordings that are compiled or reconstructed from various two-dimensional recordings. If materials are used that are radiolucent, such as plastics or certain ceramics, then good two-dimensional x-ray recordings (fluoroscopic recordings) can generally be obtained. The same does not apply to a three-dimensional image or two-dimensional recordings from which the three-dimensional image can be obtained. Artifacts can occur in these images even with materials having good radiolucent properties. It is noted that artifact creation is often not based on the density of the fastening device material but rather on differences in densities that occur in a body.

SUMMARY OF THE INVENTION

A fastening device in accordance with the invention may be manufactured (at least in part) from a material that offers advantages with regard to radiolucency and three-dimensional x-ray image artifacts. The fastening device may be formed such that it can be fastened to a body with a mechanism that resists stresses and bending.

A fastening device in accordance with the invention for fastening a reference device to a part of a body (for example, a bone) may be manufactured (at least in part) from an unsubstituted carbon fiber reinforced polyether compound, a monosubstituted carbon fiber reinforced polyether compound, or a multisubstituted carbon fiber reinforced polyether compound. Such a compound may comprise an aromatic unsubstituted carbon fiber reinforced polyether compound, an aromatic monosubstituted carbon fiber reinforced polyether compound, or an aromatic multisubstituted carbon fiber reinforced polyether compound.

The aromatic unsubstituted carbon fiber reinforced polyether compound, aromatic monosubstituted carbon fiber reinforced polyether compound, or aromatic multisubstituted carbon fiber reinforced polyether compound may comprise unsubstituted carbon fiber reinforced polyaryl ether ketones, monosubstituted carbon fiber reinforced polyaryl ether ketones, or multisubstituted carbon fiber reinforced polyaryl ether ketones, (for example, poly(ether ether ketone)s (PEEK), poly(ether ketone)s (PEK) or poly(ether ketone ketone)s (PEKK)).

BRIEF DESCRIPTION OF THE DRAWINGS

The forgoing and other features of the invention are hereinafter discussed with reference to the figures.

DETAILED DESCRIPTION

Figure 1A:
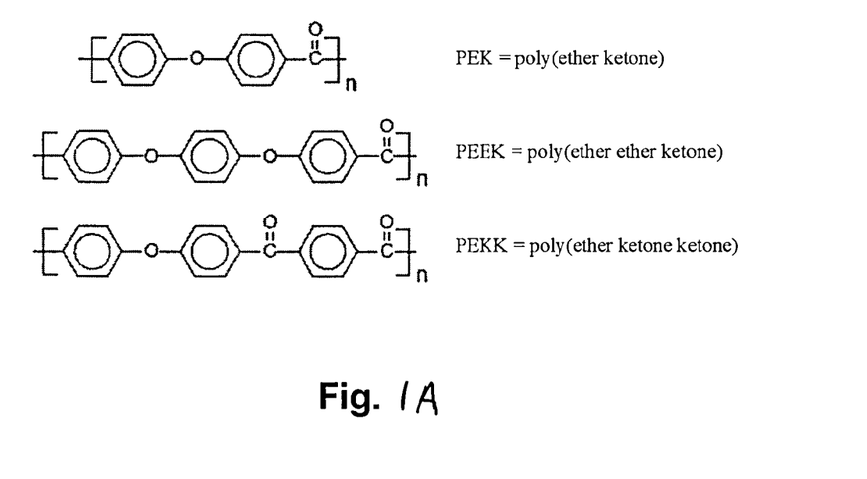
FIGS. 1A and 1B shows the nomenclature for describing polyaryl ether ketones (PEK, PEEK and PEKK) and polyether imides (PEI).

Material designations used herein, such as, PEK, PEEK and PEKK are briefly explained in the following: in a poly (ether ketone) (PEK), the main chain is made of benzene rings that are connected to each other alternately by an ether group and a keto group. An example of a PEK is shown in FIG. 1A (top). In relation to the individual benzene rings, the connections to the chain are at the 1,4 position in each case (i.e., in the para position). The connection between the individual benzene rings within the chain in the para position imbues the poly(ether ketone)s with comparatively high strength. PEEK is a polymer that is composed of a number of units, wherein each unit consists of three benzene rings that are connected to each other via a first ether bridge, a second ether bridge, and a keto bridge, respectively. An example of a PEEK is shown in FIG. 1A (middle). PEKK (i.e., poly(ether ketone ketone) is a multitude of units in which three benzene rings are connected to each other by an ether bridge, a first keto bridge and a second keto bridge, respectively. An example of a PEKK is shown in FIG. 1A (bottom). The reference "n" in FIG. 1A indicates the number of base units linked in the described manner.

Figure 1B:
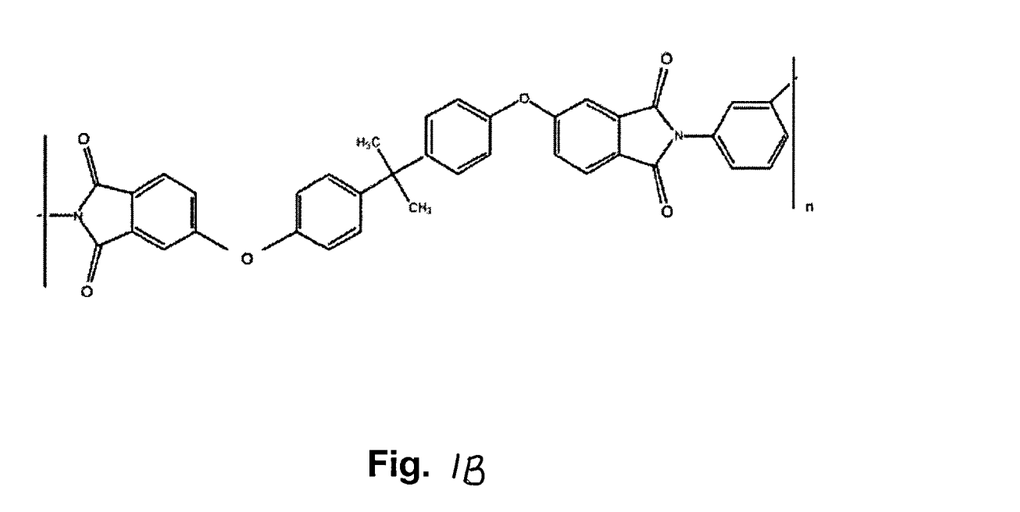

In accordance with the invention, the aromatic unsubstituted carbon fiber reinforced polyether compound, aromatic monosubstituted carbon fiber reinforced polyether compound, or aromatic multisubstituted carbon fiber reinforced polyether compound may comprise a polyether imide (PEI—a polymer in which the main chain is made of aromatic rings linked by ether and imide groups). The structure of such a polyether imide is shown in FIG. 1B. The reference "n" in FIG. 1B indicates the number of base units linked in the described manner.

In the exemplary embodiments described herein that comprise benzene rings (aromatic polyether compounds, for example, PEEK, PEK, PEKK and PEI) the benzene rings can be monosubstituted or multisubstituted. They can be substituted in the meta and/or ortho position, wherein the substitution onto a benzene ring can be identical on all the benzene rings of the polymer as a whole. The substitution onto a benzene ring also can be different on the benzene rings of the polymer as a whole.

The following substituents can be used as the substituents for both monosubstitution and multisubstitution: $C_1$-$C_8$ alkyls (for example, methyl, ethyl, propyl, butyl, pentyl, hexyl, heptyl and/or octyl groups) wherein each of the aforesaid $C_1$-$C_8$ alkyls can be linear or branched. Thus, isopropyl, sec-butyl, tert-butyl substituents and any isomers of the $C_5$-$C_8$ alkyl substituents can be used. The substituents also can be $C_2$-$C_8$ alkenyls (for example, linear or branched ethenyl, propenyl, butenyl, pentenyl, hexenyl, heptenyl and/or octenyl groups). The substituents also can be linear or branched $C_2$-$C_8$ alkinyl groups (for example, ethinyl, propinyl, butinyl, pentinyl, hexinyl, heptinyl and/or octinyl groups) which are each linear or branched. The substituents also can be $C_1$-$C_8$ alkoxyls (for example, methoxy, ethoxy, propoxy, butoxy, pentoxy, hexoxy, heptoxy and/or octoxy groups).

Other conceivable isomeric forms also can be substituted in the case of alkenyl and/or alkinyl substituents.

The substituents also can be cyclic, non-aromatic or aromatic $C_4$-$C_8$ alkyl substituents (for example, cyclobutyl, cyclopentyl, cyclohexyl, cycloheptyl or cyclooctyl radicals).

The substituents also can be chlorine, iodine and/or bromine. The substituents can include a nitro group, a hydroxyl group and/or an amino group. The substituents can include a phenyl, benzyl and/or benzoyl group.

In accordance with the invention, the aforesaid unsubstituted, monosubstituted, or multisubstituted polyether compounds may be carbon fiber reinforced. Short fibers, long fibers and/or continuous fibers may be used for carbon fiber reinforcing, wherein short fibers are defined as fibers exhibiting a length of between 0.1 and 1 mm. Long fibers are defined as fibers exhibiting a length of between 1 and 50 mm. Fibers whose length exceeds 50 mm are referred to herein as continuous fibers. The extent of the fiber reinforcement in a compound can be described by the volumetric proportion of fibers ("% vol"). In accordance with one aspect of the invention, at least a part of a fastening device includes unsubstituted carbon fiber reinforced, monosubstituted carbon fiber reinforced, or multisubstituted carbon fiber reinforced PEEK, PEK, PEKK or PEI including carbon fiber reinforcing via long fibers or continuous fibers. In one example in accordance with the invention, the carbon fiber content of the at least one part may be at or between 50 to 65 percent by volume (for example, 55 to 60 percent).

At least one part of an exemplary fastening device in accordance with the invention may include unsubstituted carbon fiber reinforced, monosubstituted carbon fiber reinforced, or multisubstituted carbon fiber reinforced PEEK, PEK, PEKK or PEI including carbon fiber reinforcing via short fibers. In this example, the carbon fiber content of the at least one part may be at or between 25 and 35% vol (for example, about 30% vol). Production tolerances may be on the order of ±0.5% vol to ±2% vol.

At least one part of an exemplary fastening device in accordance with the invention may include one of the materials described above. The fastening device may be formed from a number of parts, wherein one of these parts is made of and/or includes one of the materials described above. The at least one part of the fastening device may be composed of different materials. An example of such an arrangement can include a layered design, wherein one layer includes one the materials described above.

An exemplary fastening device in accordance with the invention may include at least one other part that includes unsubstituted, monosubstituted or multisubstituted PEEK, PEK, PEKK or PEI that is not carbon fiber reinforced. Such an example may be where certain parts of the fastening device are exposed to lower mechanical stresses.

An exemplary fastening device in accordance with the invention may be configured in the form of a clamp. A "clamp" is defined herein as an object that can secure an object from at least two sides by applying holding forces between the two sides.

In an exemplary fastening device in accordance with the invention, the clamp can be attached to a bone with "balanced tension." "Balanced tension" is defined herein as the following: when a clamp is attached to a bone, bending forces occur in addition to the normal holding forces. Balanced tension is a way to avoid these bending forces within parts in which excessive bending forces would have a noticeable negative effect. With balanced tension, forces act on parts of the clamp symmetrically. In other words the forces act with the same magnitude and symmetry such that they reciprocally equalize each other. Conventional clamps in the prior art do not incorporate balanced tension and may cause: excessive stiffness in the fastening device, mechanical deformations and inaccuracies when attaching reference devices, or oversized designs, which would not be acceptable for use.

In an exemplary fastening device in accordance with the invention, the clamp includes a clamping region and a carrier region that may comprise a transfer portion, wherein the clamping region and the transfer portion are in contact with each other. The clamping region may be adapted for fastening the clamp to a bone. During a clamping process, the interaction between the transfer portion and the clamping region may be tension-balanced as noted above. The clamping region of the clamp includes the components of the clamp that are essential to the securing and/or clamping process. These components of the fastening device are movable for secure fixation and clamping. The carrier region of the clamp includes the components that are not part of the clamping region. The part of the carrier region that is in contact with the clamping region may be designated as the transfer portion due to the interaction that occurs there. During fastening, bending forces act on the clamping region. In this respect, tensile stress occurs in the clamping region. The transfer portion of the carrier region experiences similar stress. The forces, however, are introduced symmetrically within the transfer portion and thus equalized, such that bending loads are minimized in the carrier region. The carrier region also may include a bearing portion. The clamping region may comprise two arms that each may be mounted such that they can rotate about an axis that is respectively guided through the bearing portion. The clamp may be formed such that the transfer portion symmetrically interacts with both arms simultaneously and thus causes a rotation of the arms about their rotational axes of the same magnitude but in opposite rotational directions. Accordingly, the clamp can be attached to the bone with balanced tension. In an example, the two rotational axes lie in the same plane at respectively equal distances from the end points of the respective arm of the clamping region.

In an exemplary fastening device in accordance with the invention, the bearing portion includes a main axis, the transfer portion is tapered, and the fastening device is formed such that the tapered transfer portion moves along the main axis of the bearing portion and thus rotates the arms of the clamping region.

The tapered transfer portion can have a wedge shape or can be formed in the shape of a truncated cone, wherein a "wedge shape" is defined herein as a three-dimensional shape that is tapered in at least one dimension from one end to the other end. The tapered transfer portion also can be tapered in two dimensions. The "main axis" is defined herein as the main axis having the smallest moment of inertia. In other words, it is the axis having the greatest longitudinal extension. Movement of the wedge-shaped transfer portion along the main axis of the bearing portion can be a sliding process, which can be performed by a translational movement of the wedge-shaped transfer portion in relation to the arms of the clamping region. It is possible, however, for the transfer portion to be truncated rather than wedge-shaped, wherein the relative movement would not be limited to a translational movement. A rotational movement also would be available.

In an exemplary fastening device in accordance with the invention, the transfer portion may be wedge-shaped and may include a guide for the end of each arm, wherein protrusions on the arms can slide along in the guide that is attached to the wedge-shaped transfer portion. The guide can be of a "positive shape" or a "negative shape" of a guide. In other words, the ends of the arms can engage with the guide and be inserted into it, or also can encompass it.

In an exemplary fastening device in accordance with the invention, the carrier region includes an activating portion that, when activated, moves the transfer portion. For example, the activating portion can be a screw element which, when correspondingly rotated, may be moved along a screw in an axial direction and exert a force on the transfer portion which may translationally and/or rotationally move the transfer portion.

In an exemplary fastening device in accordance with the invention, at least one penetrating body may include a silicon nitride ceramic (for example, a β silicon nitride ceramic). A "penetrating body" is defined herein as a wedge or region that, during fixation, penetrates into the body that is to be fixed. In the fixation of bones, pins and/or spikes may be used. The pins and/or spikes can have a tip and can withstand high loads. In an exemplary device, a number of penetrating bodies are provided. In an example wherein the fastening device comprises a clamp, the pins may be situated on both arms of the clamp and the silicon nitride ceramic may be a β silicon nitride ceramic. Other ceramics also may be mixed into or added to the silicon nitride ceramic or β silicon nitride ceramic.

In an exemplary fastening device in accordance with the invention, the fastening device includes at least one penetrating body that is attached to the fastening device using an anti-loss safety device. The anti-loss safety device can be a component of the fastening device that prevents penetrating bodies from remaining in the body (or bone) when the fastening device is detached. The anti-loss safety device also can prevent the penetrating bodies, once they have become loose, from becoming detached during the removal process and falling into an open incision.

In an exemplary fastening device in accordance with the invention, the anti-loss safety device includes a small plate through which the at least one penetrating body protrudes. The small plate may clamp a part of the penetrating body that does not protrude through a hole in the small plate. The small part of the body may be clamped between the fastening device and the small plate. One exemplary method of clamping the penetrating bodies is give the bodies varying diameters such that a larger diameter portion will not pass through the hole in the small plate. In other words, the penetrating bodies may be widened away from the tip incrementally or continuously, such that they do not completely pass through the small plate.

In an exemplary fastening device in accordance with the invention, the anti-loss safety device can be fastened to the fastening device using a snap lock. The snap lock can comprise small inward latching protrusions. Alternatively, the anti-loss safety device can be fastened to the fastening device with screws or adhesives.

In accordance with another aspect of the invention, the invention relates to a system including a fastening device and a reference device for computer-assisted operations. The latter can be fastened or fixed to the fastening device. The reference device may include a number of markers situated in a defined known geometric relationship to one another. The markers may include active or passive markers, wherein the markers can be detected by a camera system based on the radiation that they emit or reflect.

Figure 2:
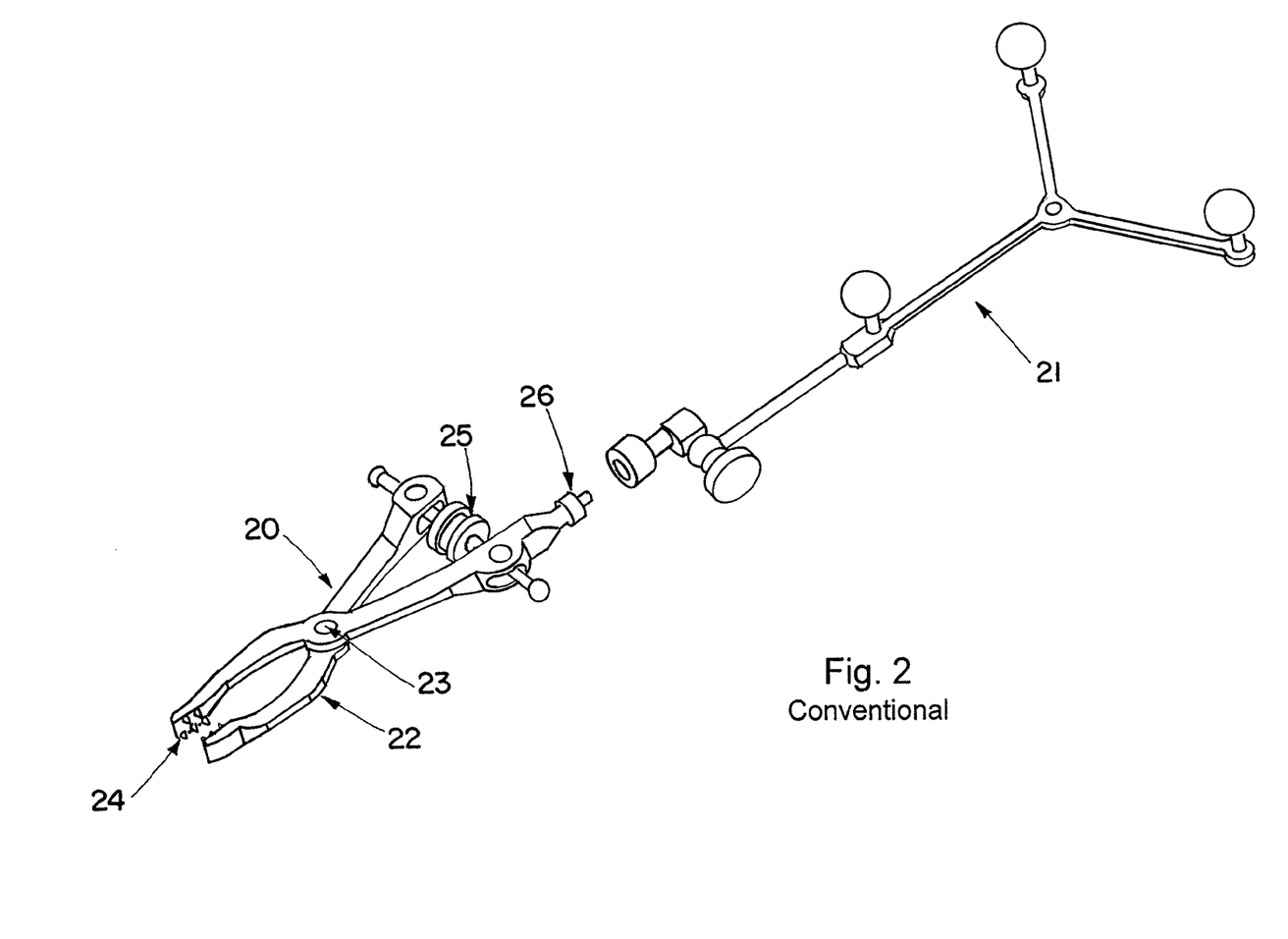
FIG. 2 shows an example of a prior art conventional clamp for securing a reference device.

FIG. 2 shows a conventional prior art clamp 20 manufactured from high grade steel to which a reference device 21 may be attached. The conventional 30 clamp 20 is not radiolucent. The clamp 20 includes two clamping jaws or arms 22 that are mounted such that they can rotate about a common axis or pin 23. At one end, the arms 22 may have spikes 24 that can penetrate into a bone. At the opposite end of the arms, a screw connection 25 between the two arms 22 may be provided. By increasing or decreasing the distance between the two ends of the arms 22 away from the spikes 24, the clamp 20 is opened or closed and tightened. The clamp 20 has an adapter 26 to which a reference device 21 can be fastened.

As noted above, the components shown in FIG. 2 (the clamp 20 and the reference device 21) consist of high-grade steel and are not radiolucent. This is not the case with a clamp in accordance with the invention, which at least partly comprises an unsubstituted carbon fiber reinforced polyether compound, a monosubstituted carbon fiber reinforced polyether compound, or a multisubstituted carbon fiber reinforced polyether compound.

Figure 3:
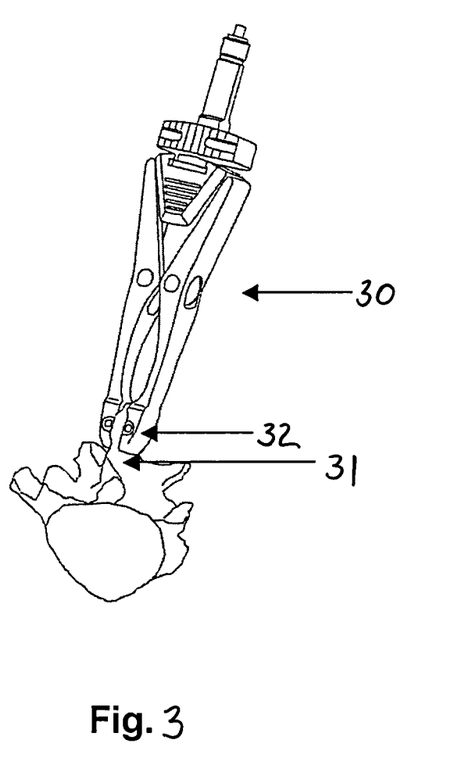
FIG. 3 shows an exemplary clamp in accordance with the invention fastened to a dorsal process of a vertebra.

FIG. 3 shows the geometry of a fastening device in accordance with the invention, which is embodied in the form of a clamp 30. The clamp 30 is fastened to a dorsal process of a vertebra 31 using two clamping jaws or arms 32.

Figure 4:
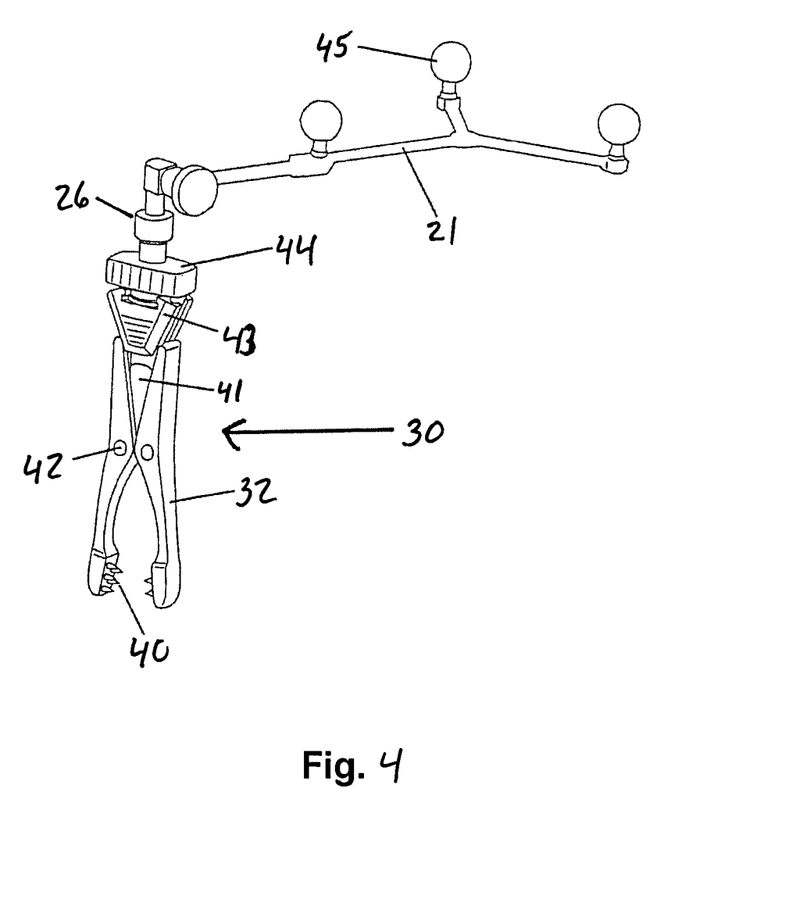
FIG. 4 shows an exemplary clamp in accordance with the invention fastened to a reference device.

FIG. 4 shows in detail the clamp 30 together with a reference device 21 that is fastened to it via an adapter 26. The reference device 21 in the figure (and in most of the test recordings mentioned herein) was manufactured from high-grade steel. A radiolucent material (for example, plastic or a certain ceramic) also may be used for the reference device 21. The clamp 30 in FIG. 4 comprises two mutually opposing arms 32 in the form of clamping jaws. Spikes 40 may be disposed at the ends of the arms 32 (which contact a bone). The spikes 40 may be manufactured from silicon nitride ceramic. The clamp 30 also includes a main rod 41 that includes two rotational axes or pins 42 upon which the arms 32 are respectively mounted. A wedge piece 43, which serves as a transfer portion, may be in contact with a turning wheel 44 that includes a screw connection to the main rod 41. Rotating the turning wheel 44 moves the wedge piece 43 downwards, hence closing the arms 32. A clamping force is transferred symmetrically onto the wedge piece 43. The arms 32 may include elements that engage with corresponding guide slits on the wedge piece 43 and are thus connected to the wedge piece 43 and which ensure that the clamping jaws automatically open when the turning wheel 44 is rotated in the opposite direction. The turning wheel 44 can be removed from the wedge piece 43 for cleaning and sterilization. An adapter 26 ensures that the reference device 21 can be attached and detached. In the example shown, the reference device 21 comprises at least three markers 45 that are situated at known, defined distances from each other.

Figure 5:
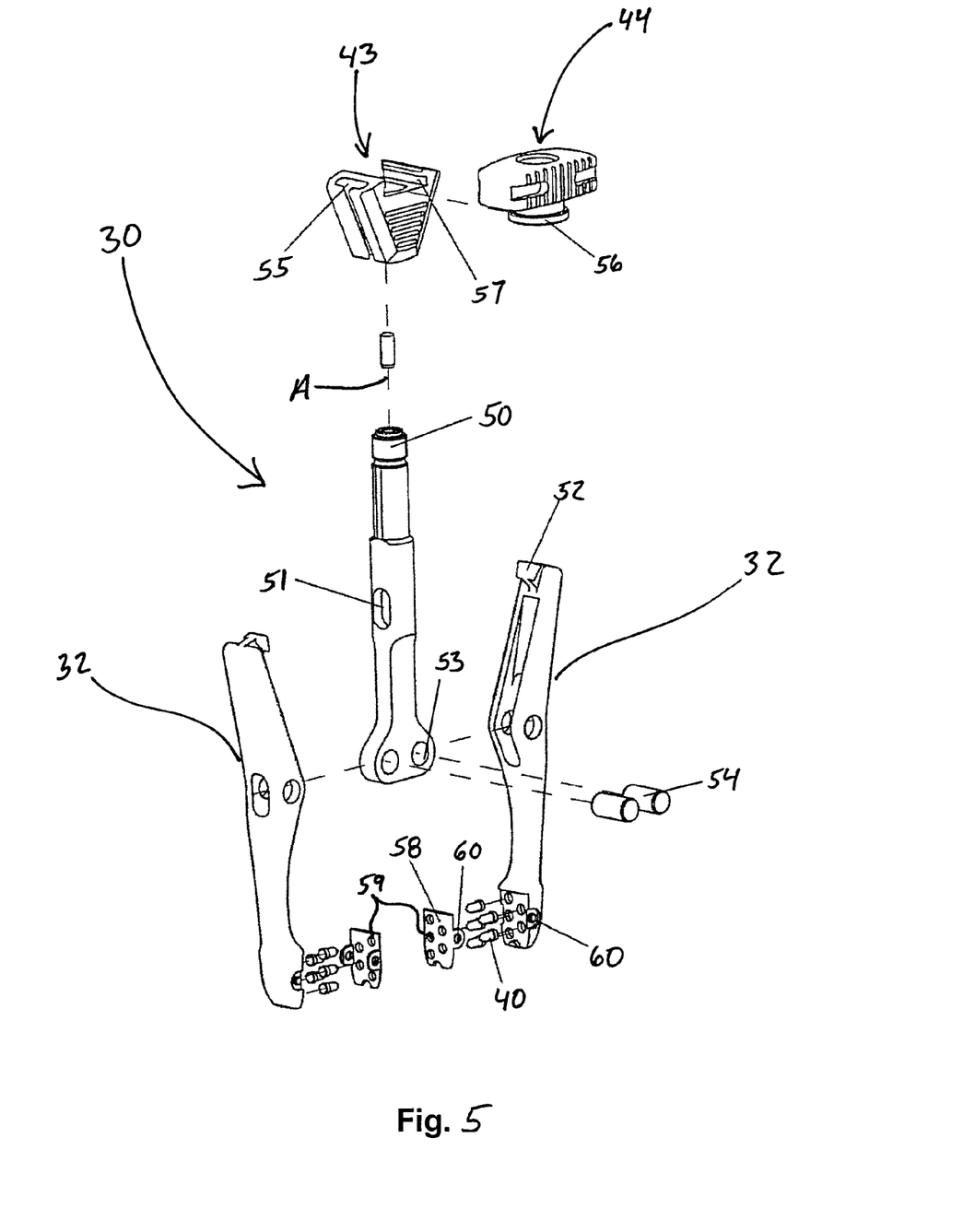
FIG. 5 shows an exploded detail view of the clamp shown in FIG. 4.

FIG. 5 shows the clamp 30 in an exploded representation and in greater detail. The design of the main rod 41 is shown in detail and is described as follows. In an upper region ("upper" and "lower" each being meant in relation to the relative position in the figure), the main rod 41 comprises a cylindrical portion 50 that includes an adapter for a reference device. The main rod 41 comprises a cavity 51 in the middle, which in the present example is formed in an oval shape. Small hooks 52 on the arms 32 can engage with said cavity 51. This engagement enables a space-saving feature of the clamp that allows a minimally invasive application of the clamp in accordance with the invention. In its lower region, the main rod 41 comprises two openings 53 into which axes or pins 54 can be located and simultaneously guided through the arms 32, such that the rotational axes for the two arms 32 are defined.

On the wedge piece 43, which serves as a transfer portion, a cavity 55 is disposed that serves as a guide for the arms 32, which engage with the wedge piece 43 via the small hooks 52. The turning wheel 44 may be secured to the wedge piece 43 by a collar 56 that may be inserted into a correspondingly formed cavity 57 in the wedge piece 43. The turning wheel 44, which serves as an activating piece, can be placed onto the wedge piece 43 and screwed onto the main rod 41. If the turning wheel 44 is activated (for example, rotated) the contact with the wedge piece 43 moves the wedge piece 43 or slides it down along the main rod 41. This action causes the arms 32 to be spread, wherein the small hooks 52 on the arms 32 slide upwards in the cavity or guide 55 of the wedge piece 43. The wedge piece 43 may be formed mirror-symmetrically with respect to an axis A. Through this process, the arms 32 and/or small hooks 52 are moved symmetrically. The force exerted by the wedge piece 43 on the arms 32 is likewise symmetrical, hence reducing bending forces on the main rod 41.

A number of spikes 40 are shown in the clamping region of the clamp 30. The spikes 40 may be pressed or adhered into the clamping arm or jaws 32. The spikes 40 are formed with a slight swelling at the end opposite their tips (i.e., the diameter of the spikes can vary). A small plate 58 may be provided with a plurality of holes 59 to slide over the spikes 40, wherein only the regions of the spikes that are provided with the smaller diameter fit through the plurality of holes 59 in the small plate 58. The swelled region of the spikes 40 may be clamped between the small plate 58 and the clamping jaw 32. The small plate 58 thus serves as an anti-loss safety device. The small plate 58 can be fastened to the clamping jaw 32 via a snap lock 60.

Figure 6:
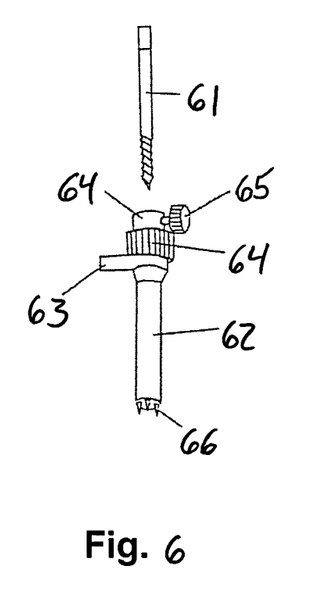
FIG. 6 shows an exemplary fastening device in accordance with the invention including a screw.
Figure 7:
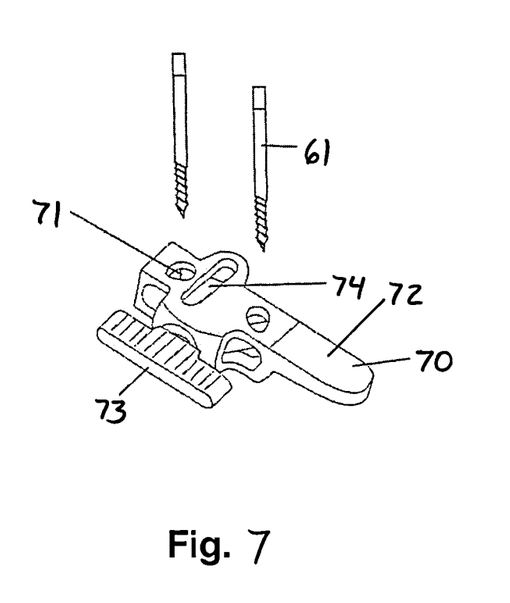
FIG. 7 shows an exemplary fastening device in accordance with the invention including two screws.

FIGS. 6 and 7 show two exemplary fastening devices in accordance with the invention. FIG. 6 shows a fastening device comprising a bone screw 61 and FIG. 7 shows a fastening device comprising two bone screws 61. The fastening devices shown have known configurations, but in the present case, they are at least partly manufactured from unsubstituted carbon fiber reinforced, monosubstituted carbon fiber reinforced, or multisubstituted carbon fiber reinforced PEEK, wherein various different types of fiber and carbon fiber volume percentage can be used, as described elsewhere herein.

In FIG. 6, the fastening device comprises a main piece 62 to which a reference device can be attached using an adapter 63. The main piece 62 is attached to a bone (not shown) via a bone screw 61 that is screwed into the bone. A small wheel 64 may be rotated to exert a force on the main piece 62. This force presses a plurality of spikes 66 into the bone structure. By using a device such as is shown, it is possible to achieve a fixed connection to the bone structure. The spikes 66 can be made of either plastic or ceramic materials.

In FIG. 7, two bone screws 61 are used to fasten a reference device to the bone structure. The screws 61 are spaced a certain distance from each other using a drill template. A main piece 70 is inserted onto two bone screws 61, which are screwed into the bone (not shown), via a pair of openings 71. The main piece 70 has an adapter 72, to which a reference device can be attached. A wheel 73 moves a wedge-shaped partial piece 74 in an interior area of the main piece 70, thus fixedly clamping the main piece 70 to the two screws 61.

Conventional fastening devices such as clamps are presently manufactured from titanium or high-grade steel. For strength and other reasons, these devices cannot be made of another material without additionally adapting the fastening device. For example, it is not possible to manufacture the clamp shown in FIG. 2 from PEEK that has not been carbon fiber reinforced. The clamp made of PEEK that is not carbon fiber reinforced would be required to be 2 to 3 times larger than the high-grade steel clamp. Otherwise, the clamp would not have the required strength. Such an increase in size is not acceptable for a fastening device that is used in computer-assisted surgery as it would obstruct the surgeon's freedom of movement and view.

A number of series of experiments were conducted using a prototype of a fastening device in accordance with the invention, to examine the artifact creation properties of the fastening device. Various recordings were taken (for example, two-dimensional x-ray tomograms and three-dimensional x-ray recordings compiled and reconstructed from two-dimensional images) with a clamp prototype as shown in FIGS. 4 and 5. The fastening device was made from the following different PEEK materials: the arms 32 and the axes or pins 54 were made from unsubstituted carbon fiber reinforced PEEK reinforced by continuous fibers with a carbon fiber content of 55 to 60 percent by volume. The main rod 41 and the wedge piece 43 were made from unsubstituted carbon fiber reinforced PEEK reinforced by short fibers with a carbon fiber content of about 30 percent by volume. The small plate 58 and the turning wheel 44 were made from unsubstituted PEEK that was not carbon fiber reinforced. The spikes 40 were made from silicon nitride ceramic.

An exemplary fastening device in accordance with the invention and in the form of a clamp may be made from different PEEK materials because the forces acting on the individual components of the fastening device differ. While significant bending forces can act on the axes or pins 54 and the arms 32, the same is not the case with the main rod 41, wedge piece 43, or turning wheel 44. Different PEEK materials may be used, wherein the material having the greatest resistance to stress and rigidity is selected for the parts that experience the greatest stresses. Moreover, the transfer of forces between the clamping region and the carrier region are tension-balanced to further reduce the mechanical stresses imposed on the components. The clamp 30 can be disassembled, cleaned, and/or sterilized and reassembled. The use of multiple materials allows different materials to be selected for different components. When selecting the material of the spikes 40, the following were considered: stability, resistance to mechanical stress, and artifact creation in two-dimensional x-ray tomograms and reconstructed three-dimensional x-ray images. Silicon nitride ceramic was selected.

Figure 8A:
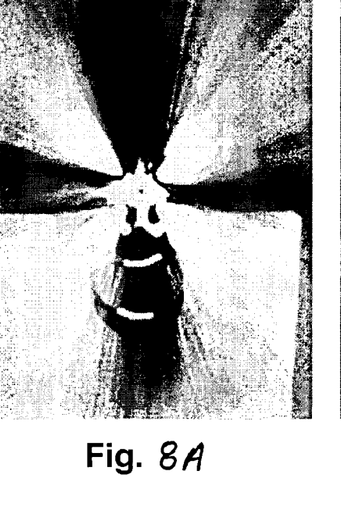
FIGS. 8A and 8B show exemplary x-ray tomograms exhibiting major artifacts created by a clamp made of high-grade steel recorded using a computer tomography.
Figure 8B:
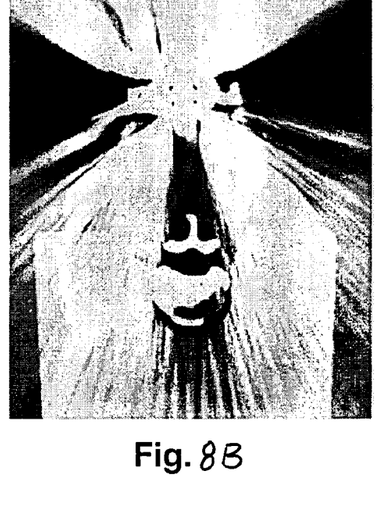

FIGS. 8A and 8B show individual baseline x-ray tomograms from a reconstructed three-dimensional x-ray model recorded using a computer tomograph. In both cases, a section through a certain vertebra of the spine was recorded, wherein a conventional clamp made of high-grade steel was fixed to a vertebra. Significant artifact formation can be seen in both FIGS. 8A and 8B. The images are superimposed with heavy black and white lines in a stellar arrangement, such that the white vertebrae in the center of the image can barely be seen. In practice, the images are unsuitable for computer-assisted operations, since relevant bone structures on the vertebra, into which screws have to be introduced using computer assistance, can no longer be identified.

Figure 9A:
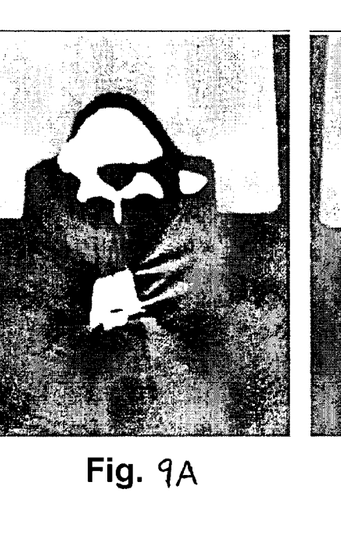
FIGS. 9A and 9B show exemplary x-ray tomograms exhibiting minor artifacts created by a clamp in accordance with the invention recorded using a computer tomography.
Figure 9B:
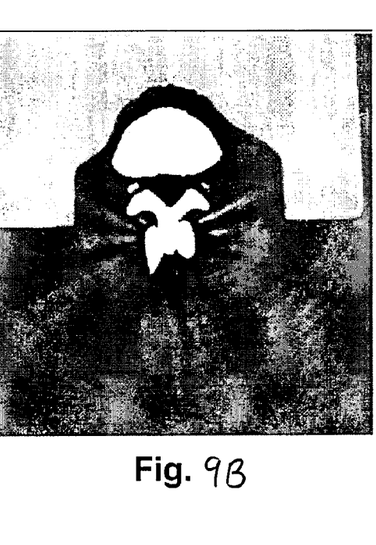

For comparison, FIGS. 9A and 9B show two different two-dimensional sections through a vertebra from a reconstructed three-dimensional x-ray model recorded using a computer tomograph, wherein a radiolucent clamp in accordance with the invention made of carbon fiber reinforced PEEK has been used. The clamp made of carbon fiber reinforced PEEK was also provided with spikes made of a silicon nitride ceramic. The spikes made of silicon nitride ceramic can withstand comparatively heavy mechanical loads. The slight artifacts that can be seen in FIGS. 9A and 9B may be the result of using the silicon nitride ceramic pins. The slight artifacts do not have a noticeable negative effect on the image quality.

Figure 10:
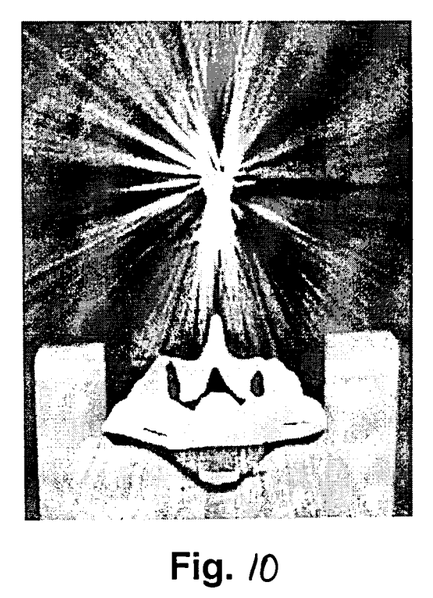
FIG. 10 shows an exemplary x-ray tomogram exhibiting artifacts created by a conventional reference device recorded using a computer tomography.

FIG. 10 shows a tomogram through a vertebra from a reconstructed three-dimensional x-ray model recorded using a computer tomograph, wherein a clamp in accordance with the invention made of carbon fiber reinforced PEEK has been used, and to which a conventional reference device consisting of high-grade steel has been fastened. The latter is situated at a considerable distance from the vertebra to which the clamp is fixed. While the artifacts caused by using the known reference device made of high-grade steel are significant, they are situated at a considerable distance from the vertebra that is of interest. If this distance is large enough, good reconstructed two-dimensional x-ray tomograms can be obtained, even when using reference devices of the prior art made of high-grade steel in combination with the clamp in accordance with the invention made of carbon fiber reinforced PEEK.

Figure 11A:
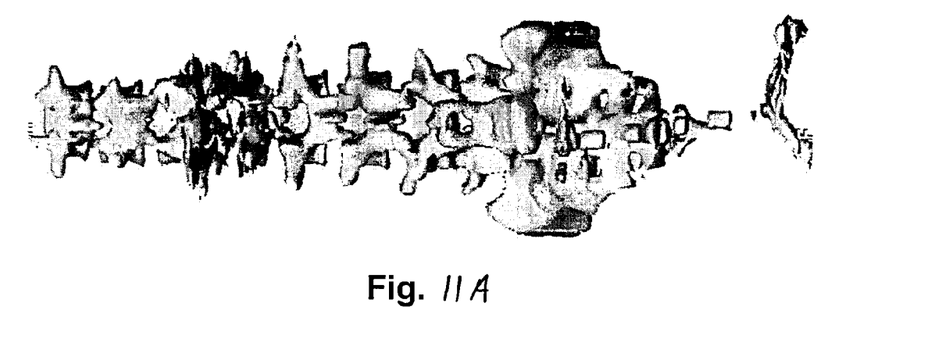
FIGS. 11A and 11B show exemplary dorsal and a lateral three-dimensional reconstructions of an x-ray image, wherein both a conventional clamp (made of high-grade steel) and a clamp in accordance with the invention (made of carbon fiber reinforced PEEK) have been imaged together for comparison of the creation of artifacts.
Figure 11B:
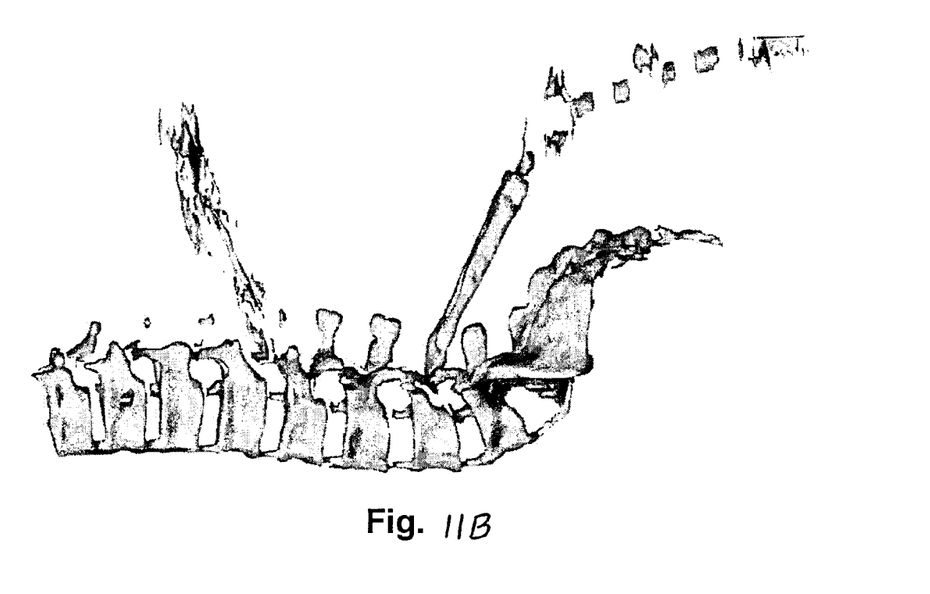

FIGS. 11A and 11B show three-dimensional reconstructions recorded using a computer tomograph, wherein FIG. 11A shows a dorsal three-dimensional reconstruction and FIG. 11B shows a lateral three-dimensional reconstruction. A clamp made of high-grade steel was again attached in the left-hand region, while the prototype in accordance with the invention was fastened in the right-hand region. Substantially more significant artifacts may be noted on the left in the region of the high-grade steel clamp, and relevant regions of the spine (for example, dorsal processes) are missing from view. In the right-hand region, however, the complete contour of the clamp can be seen and the underlying region of the spine is completely reconstructed.

Figure 12A:
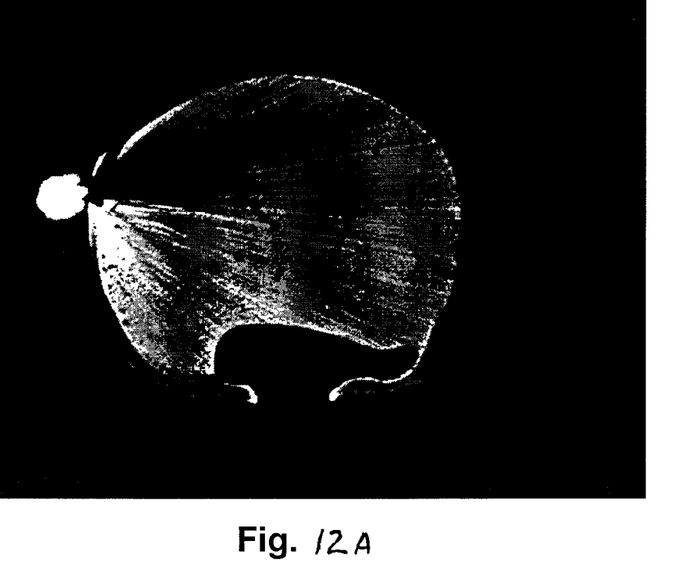
FIGS. 12A and 12B show artifacts created by a titanium pin and silicon nitride ceramic pin recorded respectively using a computer tomography.
Figure 12B:
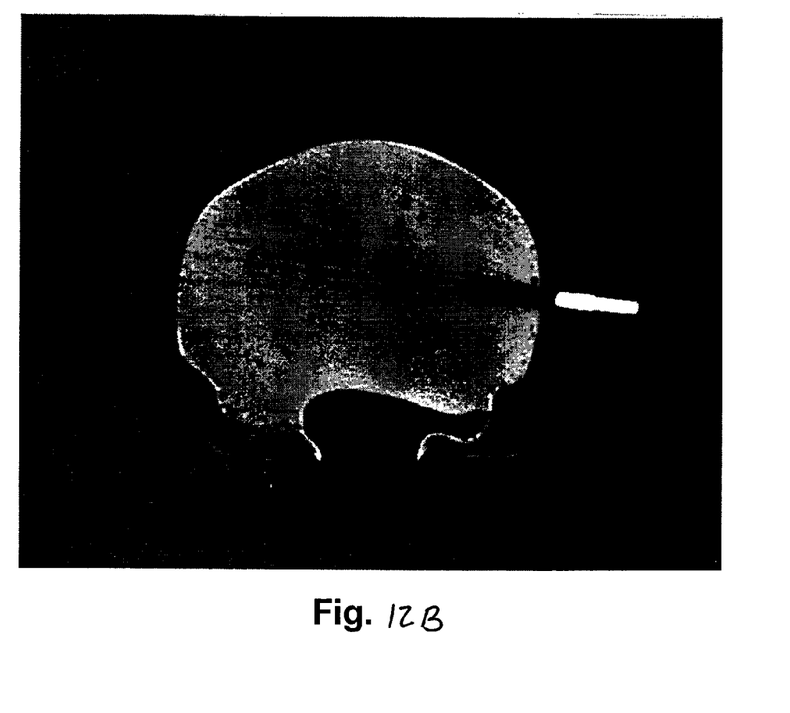

FIGS. 12A and 12B show different artifact creation properties when using a titanium pin and when using a silicon nitride ceramic pin in a three-dimensionally reconstructed x-ray tomogram. Rod-shaped test bodies made of the cited materials were used for this purpose. Significant artifacts occur when a titanium pin is used, while only minor and aligned artifacts occur when the silicon nitride ceramic pin is used.

It follows from the recordings that substantially better results with regard to artifact creation in x-ray recordings were obtained due to the choice of materials in accordance with the invention. Using a clamp made of unsubstituted carbon fiber reinforced, monosubstituted carbon fiber reinforced, or multisubstituted carbon fiber reinforced PEEK enabled x-ray recordings to be taken and three-dimensional image reconstructions to be obtained that exhibit only very minor artifacts and therefore allow a large number of details to be very clearly identified. This performance is highly advantageous for computer-assisted operations that have to be performed with a very high level of precision. Using the described carbon fiber reinforced PEEK materials simultaneously ensures a high resistance to mechanical stress and the necessary degree of miniaturization of the fastening device, thus enabling a minimally invasive application.

Although the invention has been shown and described with respect to a certain exemplary embodiment or embodiments, it is obvious that equivalent alterations and modifications will occur to others skilled in the art upon the reading and understanding of this specification and the annexed figures. For example, regard to the various functions performed by the above described elements (components, assemblies, devices, etc.), the terms used to describe such elements are intended to correspond, unless otherwise indicated, to any element that performs the specified function of the described element (i.e., that is functionally equivalent), even though not structurally equivalent to the disclosed structure that performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A fastening device for fastening a reference device to a part of a body for use in computer-assisted operations, comprising:
   a component that is at least partly made from an:
   unsubstituted carbon fiber reinforced polyether compound,
   a monosubstituted carbon fiber reinforced polyether compound, or
   a multisubstituted carbon fiber reinforced polyether compound, wherein the fastening device further comprises carbon fiber reinforcement comprising long fibers or continuous fibers,
   wherein the fastening device has the form of a clamp configured for balanced tension attachment to a bone, the clamp comprising
   a first arm having a distal end and a second arm having a second distal end, the first and second arms movable relative to each other, wherein the combination of the first distal end and the second distal end define a clamping region, wherein the first arm and the second arm are mounted such that they can rotate about a pin that is respectively guided through the bearing portion, and
   a carrier region that includes a wedge-shaped transfer portion and a bearing portion, wherein the transfer portion symmetrically interacts with the first arm and the second arm simultaneously and thus causes a rotation of the arms about their rotational axes, of the same magnitude but in opposite rotational directions, such that the clamp can be attached to the bone with balanced tensions, and
   an activating portion comprising a turning wheel which, when turned, is translated along a main axis of the bearing portion and which moves the wedge-shaped transfer portion along the main axis of the bearing portion,
   wherein the bearing portion comprises a main axis and the fastening device is configured such that movement of the wedge-shaped transfer portion along the main axis of the bearing portion causes corresponding movement of at least one of the first arm and the second arm so as to alter a spacing between the first distal end and the second distal end,
   wherein the clamping region and the transfer portion contact each other, and wherein the clamping region is configured for fastening the clamp to a bone, and wherein during a clamping process, the interaction between the transfer portion and the clamping region is tension-balanced.

2. A fastening device according to claim 1, wherein
the unsubstituted carbon fiber reinforced polyether compound,
a monosubstituted carbon fiber reinforced polyether compound, or
a multisubstituted carbon fiber reinforced polyether compound comprises;
   an aromatic unsubstituted carbon fiber reinforced polyether compound,
   an aromatic monosubstituted carbon fiber reinforced polyether compound, or
   an aromatic multisubstituted carbon fiber reinforced polyether compound.

3. A fastening device according to claim 1, wherein the unsubstituted carbon fiber reinforced polyether compound, a monosubstituted carbon fiber reinforced polyether compound, or
   a multisubstituted carbon fiber reinforced polyether compound comprises:
   unsubstituted carbon fiber reinforced (PEEK),
   monosubstituted carbon fiber reinforced (PEEK), or
   multisubstituted carbon fiber reinforced poly (ether ether ketone) (PEEK):

4. A fastening device according to claim 1, wherein
the unsubstituted carbon fiber reinforced polyether compound,
a monosubstituted carbon fiber reinforced polyether compound, or
a multisubstituted carbon fiber reinforced polyether compound comprises:
   unsubstituted carbon fiber reinforced (PEK),
   monosubstituted carbon fiber reinforced (PEK) or multisubstituted carbon fiber reinforced poly(ether ketone) (PEK):

5. A fastening device according to claim 1, wherein
the unsubstituted carbon fiber reinforced polyether compound,
a monosubstituted carbon fiber reinforced polyether compound, or a multisubstituted carbon fiber reinforced polyether compound comprises:
   unsubstituted carbon fiber reinforced (PEKK),
   monosubstituted carbon fiber reinforced (PEKK) or
   multisubstituted carbon fiber reinforced poly (ether ketone ketone) (PEKK):

6. A fastening device according to claim 1, wherein
the unsubstituted carbon fiber reinforced polyether compound,
a monosubstituted carbon fiber reinforced polyether compound, or a multisubstituted carbon fiber reinforced polyether compound comprises:

unsubstituted carbon fiber reinforced (PEI), monosubstituted carbon fiber reinforced (PEI) or multisubstituted carbon fiber reinforced polyether imide (PEI).

7. The fastening device according to claim 1, wherein the carbon fiber reinforcement content of at least one component of the fastening device comprises 50 to 65 percent by volume (% vol).

8. The fastening device according to claim 7, wherein the carbon fiber reinforcement content of at least one component of the fastening device comprises 55 to 60 percent by volume (% vol).

9. The fastening device according to claim 1, wherein the fastening device further comprises carbon fiber reinforcement comprising short fibers.

10. The fastening device according to claim 9, wherein the carbon fiber reinforcement content of at least one component of the fastening device comprises 25 to 35 percent by volume (% vol).

11. The fastening device according to claim 10, wherein the carbon fiber reinforcement content of at least one component of the fastening device comprises about 30 percent by volume (% vol).

12. The fastening device according to claim 1, wherein at least one component of the fastening device is made from an unsubstituted, monosubstituted or multisubstituted polyether compound that is not carbon fiber reinforced.

13. The fastening device according to claim 1, wherein the at least one component of the fastening device is made from an unsubstituted, monosubstituted or multisubstituted polyether compound that is not carbon fiber reinforced comprises unsubstituted, monosubstituted or multisubstituted PEEK, PEK, PEKK or PEI.

14. The fastening device according to claim 1, wherein the wedge-shaped transfer portion comprises a guide for the end of each arm.

15. The fastening device according to claim 1, comprising at least one penetrating body that comprises a silicon nitride ceramic.

16. The fastening device according to claim 15, wherein the at least one penetrating body comprises a β silicon nitride ceramic.

17. The fastening device according to claim 1, comprising at least one penetrating body that is attached to the fastening device via an anti-loss safety device.

18. The fastening device according to claim 17, wherein the anti-loss safety device comprises
   a small plate which the at least one penetrating body partly protrudes through, and wherein
   the small plate clamps a part of the penetrating body, and wherein the part of the penetrating body does not protrude through the small plate.

19. The fastening device according to claim 17, wherein the anti-loss safety device is fastened to the fastening device via a snap lock.

* * * * *